United States Patent [19]

Nasu

[11] Patent Number: 4,983,409

[45] Date of Patent: Jan. 8, 1991

[54] ION WATER FOR PRODUCTION OF FOODS AND BEVERAGES

[76] Inventor: Atsushi Nasu, 99 Katako, Youkaichiba-shi, Chiba-ken, Japan

[21] Appl. No.: 498,213

[22] Filed: Mar. 23, 1990

[30] Foreign Application Priority Data

Apr. 3, 1989 [JP] Japan ................................. 1-84534
Aug. 17, 1989 [JP] Japan ................................. 1-211885

[51] Int. Cl.$^5$ .............................................. A23L 2/00
[52] U.S. Cl. ...................................... 426/66; 426/74
[58] Field of Search ........................... 426/66, 74, 590

[56] References Cited

U.S. PATENT DOCUMENTS 879,843  2/1908  Wallerstein ........................... 426/66

FOREIGN PATENT DOCUMENTS 56-93888  7/1981  Japan .................................... 426/66

Primary Examiner—George Yeung

[57] ABSTRACT

Ion water for the production of beverages and foods obtained by acidifying sea water, adding a strong alkali agent to make the pH high, removing the precipitate thereby formed, concentrating the resulting solution and cooling, and thereafter dissolving a precipitate formed on cooling in water, optionally further dissolving a solid obtained by removing the water content from the solution after the removal of the precipitate formed on cooling. An activated calcium material obtained by calcining animal bones at high temperatures and grinding and mainly comprising calcium phosphate may also be added. By using such ion water, the treated beverages and foods enjoy better storability, resistance to decomposition and taste, and provide the body with the essential minerals such as calcium, potassium, magnesium, silicon etc.

5 Claims, No Drawings

ION WATER FOR PRODUCTION OF FOODS AND BEVERAGES

BACKGROUND OF THE INVENTION

1. Field of the Invention

The present invention relates to ion water for use in the production of beverages and foods, and more specifically, it relates to ion water utilizing salt separated from sea water.

2. Related Art Statement

For example, the production of bread and noodles has been heretofore conducted by adding a considerably great amount of salt. The reasons for the addition of salt are as follows:

(1) Gluten contained in flour etc. imparts tackiness and elasticity when it absorbs water and swells. And when the swollen, gluten encounters inorganic matter, it shrinks and becomes firm and solid. In other words, salt helps to make noodles with the so-called strong body.

(2) It prevents the generation of cracks otherwise liable to occur during the drying step.

(3) It inhibits enzyme activity. Therefore, it can prevent a gradual reduction in elasticity.

(4) It has a bacteriostatic action.

(5) It imparts a salty taste.

When bread is produced, it is inevitable to use salt. Bread is produced by kneading flour with salt, sugar, edible oil, water etc., allowing to stand for swelling with carbon dioxide, and baking. The role of salt is mainly for improving the glutinousness. By including the carbon dioxide gas which effects swelling with formation of thin films of gluten, voluminous, tasty bread may be finished. Further, other roles of salt added to bread are to control the fermentation of yeast, and to impart salty taste enhancing the flavor of bread.

Overconsumption of salt causes various diseases, such as hypertension, heat diseases, cerebral hemorrhage etc., and it is advised that the daily intake of salt should not be more than 5 g.

Since noodles contain a considerable amount of salt, it is not desirable to eat a great amount of noodles when the reduction of the intake of salt is intended.

Further, various additives including salt water, are considered undesirable for health. In any case, it is regarded as best if we could avoid using them.

Back to the prior art processes for the production of noodles, if salt or salt water is not used, it is impossible to produce noodles which retain the good taste and mouthfeel for a predetermined time and still do not go bad.

This case also applies to bread. The production of bread requires the use of salt in an amount as great as 1-3% by weight based on the flour.

Furthermore, since water for emergency, water for whisky-and-water etc. have been packed in cans and bottles, they inevitably became very expensive and it was impossible to make them readily available in great volumes. In addition, they required a considerably large space for storage.

If calcium is insufficient, it is believed that not only bones, teeth etc. are weakened but also various diseases such as kidney disease etc. are brought about.

The tendency to eat acidic foods is believed to lead to various diseases, and it is well recognized that foods rather alkaline are good for the health.

Recently, the role of silicon in vivo, in particular, its influence exerted on the metabolism of mineral elements, phosphorus etc. in vivo, has been attracting attention, and it has been reported that with those living in regions abundant in silicon content in potable water, the blood calcium content has been increased more than normal.

Silicon is present abundantly in nature as quarts minerals which are utilized in various fields, but silicon in the sea water is present as orthosilicic acid ions or monosilicic acid ions which have been hardly utilized.

SUMMARY OF THE INVENTION

The above-described drawbacks in the prior art have been successively eliminated by the present invention.

The present inventors have been intensively studying on the separation and utilization of various elements contained in sea water, and have discovered that salt containing considerable amounts of potassium magnesium, silicon etc. may be separated by the prescribed method (Japanese Patent Application No. 201578/1987), and by utilizing such a salt, the problems of the above-described prior art food additives, stored water etc. may be solved. Accordingly, an object of the present invention is to provide ion water for the production of beverages and foods which, when applied to various beverages and foods, not only enhances the storability and antiseptic properties of said beverages and foods and improves the tastes of said beverages and foods but also enables the human body to ingest the required calcium, potassium, magnesium, silicon etc.

The ion water for the production of beverages and foods achieving the above-described object according to the present invention is selected from (1) that obtained by acidifying sea water, then adding a strong alkali agent to make the pH high, removing a precipitate (a) thus formed, then concentrating the resultant solution after the removal of said precipitate and then cooling, and thereafter dissolving a precipitate (b) formed on cooling in water, (2) that obtained by acidifying sea water, then adding a strong alkali agent to make the pH high, removing a precipitate (a) thus formed on this, then concentrating the resultant solution after the removal of said precipitate and then cooling, then removing the water content from said solution after the removal of a precipitate (b) formed on cooling to obtain a solid (c), and dissolving the precipitate (b) and the obtained solid (c) in water, and (3) ion water for the production of beverages and foods as described in (1) or (2), which further contains an activated calcium material mainly comprising calcium phosphate and obtained by calcining animal bones at high temperatures and grinding.

DETAILED DESCRIPTION OF PREFERRED EMBODIMENTS

The method for separating the precipitate (b) and the solid (c) from sea water is described below in detail.

First, sea water is adjusted to a low pH with a strong acid containing sulfate ions.

As the strong acid containing sulfate ions, dilute sulfuric acid of e.g. several % may be used, but it is also possible to use an aqueous solution obtained by adding 3-5% of conc. sulfuric acid to an aqueous solution containing activated calcium phosphate dissolved therein and removing a precipitate (hereinafter referred to as P-S acid). This P-S acid exhibits strong acidity of about pH 2.0, but in contrast to violent chemicals such as sulfuric acid, it does not harm the skin upon contact and can be used as a highly safe acid. By adding dil. sulfuric acid or P-S acid to sea water in an amount of several % and leaving for 2-3 hours, the pH of sea water may be adjusted to as low as pH 2 or below. At this time, there is almost no precipitate produced, but slight precipitates if formed may be removed together with suspended matters present in the starting sea water by means such as filtration.

Thereafter, a strong alkali agent is added to such a low pH-adjusted sea water to make the pH high. That is, the sea water once adjusted to a low pH is neutralized and further brought to a high pH, thereby salts, e.g. sulfates etc. of the alkaline earth metals and other metals which have lower solubility in high pH ranges are caused to precipitate. As such a strong alkali agent, sodium hydroxide per se may be used and also sodium hydroxide added to an aqueous solution of calcium oxide (hereinafter referred to as Ca-Na aqueous solution) etc. may be used.

A sufficient amount of the strong alkali agent is that amount which can achieve the above-described object or more, and in general 3% based on sea water in the case of sodium hydroxide (solid) or about 5% in, the case of Ca-Na aqueous solution. The alkali is added and the solution left to stand for 10 hours or longer. By this step, the sea water will have a pH 13 or higher, and a precipitate (a) is formed. This precipitate (a) is removed by filtration etc., and the remaining sea water is heated to evaporate water and thereby appropriately concentrate This concentrate is cooled to induce formation of a precipitate (b), and this precipitate (b) is separated by filtration etc. The degree of concentration is to 20 vol. % or less, preferably about 10-15% vol. %, based on sea water before concentration.

The thus obtained precipitate (b) was revealed as the result of elementary analysis to be an alkaline substance mainly containing Na, Mg, K and Ca and also a considerable amount of Si and was found to give a pH 13.5 or so when dissolved at 10% in water.

TABLE 1

| Unit (mg/kg) | | | | | |
|---|---|---|---|---|---|
| Ca | 2030 | Al | 33.5 | Mn | 1.39 |
| K | 4470 | B | 169 | Si | 697 |
| Mg | 6.10 (%) | Cr | 2.78 | Sr | 194 |
| Na | 33.7 (%) | Cu | 5.66 | Zn | 2.09 |
| S | 3.81 (%) | Fe | 17.8 | Li | 8.93 |

The solid (c) may be obtained by removing the water content from the filtrate remaining after the removal of the precipitate (b). The removal of the water content is desirably evaporation effected by heating under reduced pressure. The thus obtained solid (c) contains the elements set forth in Table 2, mainly comprising salts of sodium (NaCl, $Na_2SO_4$, $NaHSO_3$ etc.), hydroxide, oxide thereof etc., and is a strongly substance exhibiting pH 14 or higher when dissolved in water.

TABLE 2

| Unit (wt %) | | | |
|---|---|---|---|
| Na | 46.2 | Al | 0.08 |
| K | 1.2 | Ti | 0.012 |
| B | 0.015 | Br | 0.20 |
| Si | 0.48 | Cl | 26 |
| S | 2.5 | | |

The first ion water for the production of beverages and foods according to the present invention may be obtained by dissolving this precipitate (b) in water. The amount to be dissolved in this case varies depending on the beverage and food to be applied, but in general, a stock solution is prepared by dissolving, for example, about 100 g in 1 liter of water to make the pH about 13.5, and this stock solution is used by diluting according to the application. When used for the production of noodles, ion water obtained by diluting this stock solution about 20 times to pH about 10 is used. In the case of stored water or water for whisky-and-water, it is diluted about 100 times or so and used as stored water or water for whisky-and-water and such.

The second ion water according to the present invention is that obtained by dissolving the precipitate (b) and the solid (c) in water. The solid (c) herein used function as a pH adjusting agent rather than an ion source in the ion water of the present invention. That is, calcium ion water obtained by dissolving the above-described precipitate (b) in water (Japanese Patent Application No. 84534/1989) or calcium ion water obtained by dissolving activated calcium phosphate in water (Japanese Patent Publication No. 61079/1985) contains ions useful for the body such as Ca, K, Mg, Si etc., but it sometimes happened that the pH of about 13.5 at the time of preparation decreased with time. Therefore, there is no problem when it is used as potable water, but if used as ion water for which the predetermined pH is required, for example, for production of noodles, the purification of oils, the pH adjustment of foods etc., the stability of the pH is required. By using the precipitate (b) and the solid (c) in combination, ion water excellent in stability of the pH may be obtained.

Although the proportion and amounts of the precipitate (b) and the solid (c) vary depending on the application of the water, the proportion of both is suitably about 5:5-10:1 in weight ratio. Further, the amount used is such that, for example, where used as a pH-adjusting agent or for the purification of oils, a stock solution of pH 13-14 having a total content of the precipitate (b) and the solid (c) of 10% is prepared beforehand, and used. Where used for the production of noodles, ion water of pH about 10 obtained by diluting the stock solution about 20 times is used. Further, in the case of stored water or water for whisky-and-water, it is diluted about 100 times and used as stored water or water for whisky-and-water.

This ion water is diluted appropriately, and then may be mixed with flour or buckwheat flour in place of salt or salt water to produce noodles, such as wheat vermicelli, spaghetti, chinese noodles etc. The thus prepared noodles become stronger and have improved taste and mouthfeel and moreover do not so easily go bad as compared with the case where salt or salt water is used.

This ion water may also be used as water for the production of bread. Also in this case, the taste is better and it is also possible to produce salt-reduced bread by reducing the amount of salt used.

Further, this ion water may be used as stored water for emergency free from a fear of going bad for a long time even without special preserving means such as canning etc. Furthermore, such water contains potassium, magnesium, calcium, silicon etc. and therefore, it becomes very "tasty water".

This ion water may also be employed for the addition to seasoning agents, for whisky-and-water, etc.

Accordingly, the beverages and foods prepared by using this ion water have increased contents of potassium, magnesium and silicon.

Especially as described hereinbelow, by using in combination with a calcium ion material, the metabolism of calcium, potassium, magnesium etc. in vivo may be enhanced.

Further, this ion water enhances the resistance to decompose of the beverages and foods to which it has been added by its appropriate pH and the effect of the contained ions, thereby making them better preserved.

Now, the third ion water obtained by adding a calcium material to the above-described ion water will be described below.

Such an ion water (3) may be obtained by dissolving a specified calcium material and the precipitate (b) obtained from the above-described sea water in water. This ion water (3) may further contain the solid (c).

Here, the calcium material may be obtained by the following production process. Bones of e.g. cow, pigs, sheep etc. are calcined at high temperatures to remove the flesh and fat, and thereafter chopping to make bone pieces. These bone pieces are burned at 100° C. or higher for 40–50 minutes. They are ground to about 120 mesh as a standard to obtain a finished product.

The ingredients of this finished product are, although slightly varying, more or less the same as shown in Table 3. All the values are by weight in 100 g of the sample.

TABLE 3

| Phosphorous | 17.89 g |
| Calcium | 40.28 g |
| Magnesium | 679.2 mg |
| Potassium | 14 mg |
| Iron | 0.34 mg |
| Sodium | 660 mg |

Such a calcium material can produce a calcium ion water of pH about 13 by dissolving it in water to saturation.

The third ion water according to the present invention is that obtained by dissolving such a calcium material and the precipitate (b) and the solid (c), and in general, it may be obtained by adding 5–10% of a powdered calcium material to the first or second ion water and dissolving, or appropriately mixing a saturated solution of the calcium material with the first or second ion water. Where the powdered calcium material is dissolved directly, it has been confirmed that it is dissolved better as compared with the case where the powdered calcium material is dissolved in ordinary water. It may be applied to various beverages and foods by appropriately diluting as needed. It is needless to say that the necessary amounts of the calcium material, the precipitate (b) and the solid (c) may be dissolved in the predetermined amounts of water respectively according to the application.

The mixing ratio and the degree of dilution of the calcium material (or its aqueous solution) to the precipitate (b) and the solid (c) (or their aqueous solution) are appropriately selected depending on the application.

As is clear from the above description, it is possible to provide ion water containing elements believed to be good for the body according to the present invention. Especially, the ion water of the present invention contains such elements as potassium, magnesium etc. and a considerable amount of silicon, and therefore, these elements are easily ingested into the body. Further, by applying the ion water of the present invention to beverages and foods, beverages and foods excellent in storability and having good taste may be obtained by the actions of the above-described elements.

The ion water of the present invention may be prepared by using the solid powder according to the application, it may be easily transported and prepared, and thus has a high commercial value. Further, even when stored for a prolonged period of time, the fluctuation in pH is extremely low, and thus it is suitable for applications requiring a predetermined pH.

The above-described ion water may further contain other basic calcium materials for the purpose of adjusting the pH. Such calcium materials include that obtained by calcining a natural calcium material mainly comprising calcium carbonate, such as shells of e.g. scallops etc. at high temperatures such at 1000° C. or higher, and thereafter grinding. Such calcium materials are extremely inexpensive because they may be obtained by merely calcining a starting material of shells abundantly obtainable at free cost as industrial wastes and they give a high pH value when dissolved in water. However, such calcium materials have a drawback that when added to beverages or foods, they bring about bitter taste, puckery taste and odor and, further they have another drawback that for example when added to noodles etc., they cause discoloration.

Therefore, when used for noodles, stored water, soya sauce etc., it is desired that the amount added is restricted within 10% of the total calcium material used. When used for purification of oils, such as lard, fish oils etc., about 20–30% may be added. Such ion water may be especially utilized as a pH adjusting agent for foods.

(Examples)

Ten liters of P-S acid was added to 500 ml of sea water, then left to stand for 3 hours, and thereafter the insoluble matter was removed by filtration. By this, the sea water became pH 1.6. Thereafter, 15 kg of sodium hydroxide was added to 500 l of the pH-lowered sea water, and left to stand for 10 hours. At this time, 10 liters of the sea water remaining after the filtration of the formed insoluble matter was heated to reduce the water content to obtain 1.5 l of a concentrated solution. This concentrated solution was rapidly cooled to cause a precipitate, which precipitate dried to obtain 200 g of a solid (b).

On the other hand, the filtrate remaining after the removal of the precipitate was heated under reduced pressure to obtain 300 g of a solid (c).

100 g of this solid (b) was dissolved in one liter of water to obtain a stock solution of the first ion water. The results of the elementary analysis of this ion water stock solution are shown in Table 4.

50 g of the above-described solid (b) and 50 g of the solid (c) were dissolved in one liter of water to obtain a stock solution of the second ion water. These ion water stock solutions have been confirmed safe for the use in beverages and foods by analysis by the Pharmaceutists' Center of Chiba Prefecture.

TABLE 4

| Element | (ug/g) |
| --- | --- |
| Si | 24 |
| Ca | 6.7 |
| Fe | 0.03 |
| Mg | 0.20 |
| Na | 36000 |
| K | 200 |

On the other hand, 25 kg of a calcium material which was a calcined product of bones and 0.5 kg of a calcium material which was a calcined product of shells were dissolved in 10 l of water to obtain a stock solution of calcium ion water.

EXAMPLE 1

A mixture of the first ion water and the calcium ion water at a ratio of 1:1 was further diluted 20 times to prepare ion water for the production of noodles.

This ion water was added to flour at 35%, and made into noodles by mixing on a mixer in a conventional manner without using any salt. These boiled noodles were stored at a storage temperature of 4° C. for 8 days, and the number of live bacteria was examined. As a result, even after 8 days from the production, there was no increase in the number of bacteria, thus showing high storability. Further, as the result of the elemental analysis, these noodles were determined to contain great amounts of K, Ca and Mg.

EXAMPLE 2

A stock solution of the second ion water was prepared, and the pH was examined about 30 days and 60 days after the preparation, to determine that the a pH of was unchanged and it indicated pH 13.5 the same as that at the time of preparation. This stock solution was diluted about 100 times to prepare potable ion water of pH 8.3. This potable ion water was free from bleaching powder odor characteristic of tap water and thus became tasty water. As the result of its drinking test, 50 among 100 panelists evaluated it as very tasty while the remaining 50 evaluated it as tasty. Also when applied to tea, coffee etc., the results were favorable, and further, when prepared into ice, the product was hard to melt a compared with ice prepared from ordinary water, and the density and the transparency were also higher than usual. When this ice was used in whisky etc., it made whisky tasty.

EXAMPLE 3

Rice was polished, and when the rice still maintained the heat of polishing, ion water which had been obtained by diluting the ion water stock solution 20 times was sprayed or scattered on rice in an amount of 5% based on the rice while the rice was being stirred, then, after leaving to stand for 30 minutes, the rice was dried well, and the water content was made the same as before. This rice was boiled without using salt, and rice balls were prepared, and the taste and the decomposition conditions were compared with ordinary rice balls. As a result, the ordinary rice balls gave odor after one day, but those treated with the ion water did not cause any odor. Further, as regards the taste, those prepared from the untreated rice showed a difference in taste between the kinds of rice used whereas those treated with the ion water, the tackiness and the sugary taste were as good as those of first-grade rice regardless of the kind of rice. The results of the analysis of the rice treated with the ion water are shown in Table 5.

TABLE 5

| | |
|---|---|
| Calcium | 5 mg/100 g |
| Iron | 0.4 " |
| Sodium | 4 " |
| Potassium | 88 " |
| Magnesium | 30 " |

EXAMPLE 4

Ion water for the production of noodles was obtained by mixing the second ion water stock solution and the calcium ion water at a ratio of 1:10 and further diluting it 20 times.

This ion water was added to flour at 35%, and made into noodles by mixing on a mixer without using salt. These boiled noodles were left to stand at room temperature and compared with commercial boiled noodles (those prepared by using salt and sodium malate as a preservative). Although the commercial boiled noodles started to decompose 3 days after the preparation, the boiled noodles of the present example using ion water alone did not decompose even 4 day later.

What is claimed is:

1. Ion water for the production of beverages and foods which is obtained by:
    acidifying sea water;
    adding a strong alkali agent to said acidified sea water to raise the pH and to form a precipitate (a);
    removing said precipitate (a) and concentrating and cooling the remaining solution to form a precipitate (b); and
    dissolving said precipitate (b) in water to form said ion water.

2. Ion water for the production of beverages and foods in accordance with claim 1 obtained by dissolving in water an activated calcium material, which consists of calcium phosphate and is obtained by calcining animal bones at high temperatures, along with said precipitate (b).

3. Ion water for the production of beverages and foods which is obtained by:
    acidifying sea water;
    adding a strong alkali agent to said acidified sea water to raise the pH and to form a precipitate (a);
    removing said precipitate (a) and concentrating and cooling the remaining solution to form a precipitate (b); and
    dissolving in water said precipitate (b) formed on cooling and also a solid (c) obtained by removing the water from the solution remaining after the removal of said precipitate (b) to form said ion water.

4. The ion water for the production of beverages and foods according to claim 3 wherein the weight ratio of said precipitate (b) to said solid (c) is 1:1 or more.

5. Ion water in accordance with claim 3 wherein an activated calcium material, which mainly comprises calcium phosphate and is obtained by calcining animal bones and grinding, is dissolved together with the precipitate (b) and the solid (c) to form the ion water.

* * * * *

UNITED STATES PATENT AND TRADEMARK OFFICE
CERTIFICATE OF CORRECTION

PATENT NO. : 4,983,409          Page 1 of 2
DATED     : January 8, 1991
INVENTOR(S) : Atsushi NASU It is certified that error appears in the above-identified patent and that said Letters Patent is hereby corrected as shown below:

Col. 2, line 11, after "which" insert --hitherto--;

line 42, delete "on"; and line 43, delete "this".

Col. 3, line 23, after "general" insert --is--;

line 24, after "in" delete the comma ",";

line 31, after "trate" insert a period --.--;

line 56, after "strongly" insert --alkaline--.

Col. 4, line 14, "function" should read --functions--;

line 28, delete "the", second instance;

line 35, after "the", first instance, insert --ion--.

Col. 6, line 19, after "wastes" insert a comma --,--; and line 44, delete "precipate" and insert --precipitate was--.

UNITED STATES PATENT AND TRADEMARK OFFICE
CERTIFICATE OF CORRECTION

PATENT NO. : 4,983,409           Page 2 of 2

DATED : January 8, 1991

INVENTOR(S) : Atsushi NASU

It is certified that error appears in the above-identified patent and that said Letters Patent is hereby corrected as shown below:

Col. 8, line 36, after "consists" insert --mainly--.

Signed and Sealed this

Thirtieth Day of June, 1992

*Attest:*

DOUGLAS B. COMER

*Attesting Officer*      *Acting Commissioner of Patents and Trademarks*